(12) United States Patent
Wolf et al.

(10) Patent No.: US 9,545,277 B2
(45) Date of Patent: Jan. 17, 2017

(54) BONE PLATE

(71) Applicant: DePuy Synthes Products, LLC, Raynham, MA (US)

(72) Inventors: Stefan Wolf, Zuchwil (CH); This Aebi, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 177 days.

(21) Appl. No.: 14/204,967

(22) Filed: Mar. 11, 2014

(65) Prior Publication Data

US 2015/0257802 A1    Sep. 17, 2015

(51) Int. Cl.
*A61B 17/80* (2006.01)

(52) U.S. Cl.
CPC ........... *A61B 17/8061* (2013.01); *A61B 17/80* (2013.01); *A61B 17/8057* (2013.01)

(58) Field of Classification Search
CPC .. A61B 17/80; A61B 17/8061; A61B 17/8057
See application file for complete search history.

(56) References Cited

U.S. PATENT DOCUMENTS

| | | | |
|---|---|---|---|
| 5,733,287 A * | 3/1998 | Tepic | A61B 17/80 606/280 |
| 2009/0088767 A1 | 4/2009 | Leyden et al. | |
| 2010/0262193 A1 | 10/2010 | Frigg et al. | |
| 2011/0093016 A1 | 4/2011 | Aferzon | |
| 2011/0295324 A1 | 12/2011 | Donley et al. | |
| 2013/0211459 A1 * | 8/2013 | Horan | A61B 17/8052 606/280 |
| 2013/0238034 A1 | 9/2013 | Graham | |
| 2014/0066998 A1 | 3/2014 | Martin | |

FOREIGN PATENT DOCUMENTS

| | | |
|---|---|---|
| EP | 0684017 | 11/1995 |
| EP | 1741397 | 1/2007 |
| EP | 2559394 | 2/2013 |
| WO | 2013/021033 | 2/2013 |

* cited by examiner

*Primary Examiner* — Andrew Yang
(74) *Attorney, Agent, or Firm* — Fay Kaplun & Marcin, LLP

(57) ABSTRACT

A bone plate having a first, bone-facing surface and an opposing second surface has an elongate shaft portion and a head portion that is shorter and wider in comparison thereto, with at least one through hole extending through the bone plate from the first surface to the second surface in the shaft portion. The through hole comprises a variable-angle portion with a hole axis configured to receive a threaded head of a locking screw therein at a desired angle within a permitted range of angulation relative to the hole axis. The second surface has at least one depression which extends therein along a portion of the second surface between the side wall and the through hole, the depression extending about a periphery of the through hole.

16 Claims, 5 Drawing Sheets

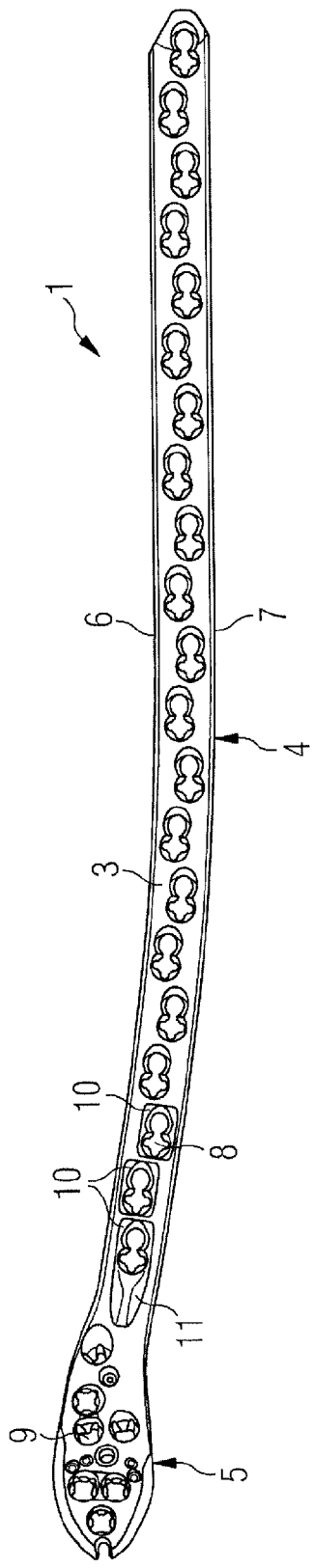
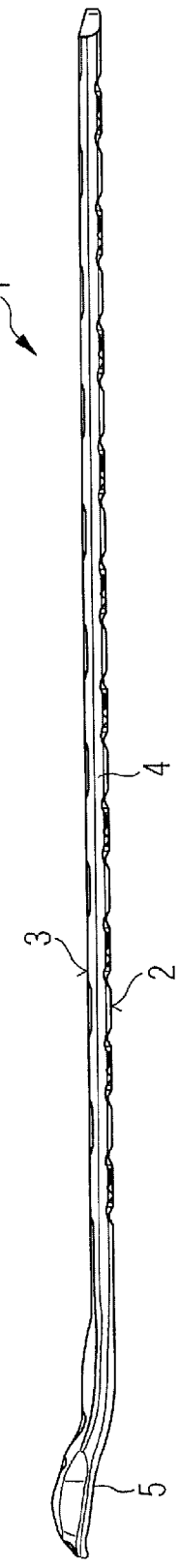
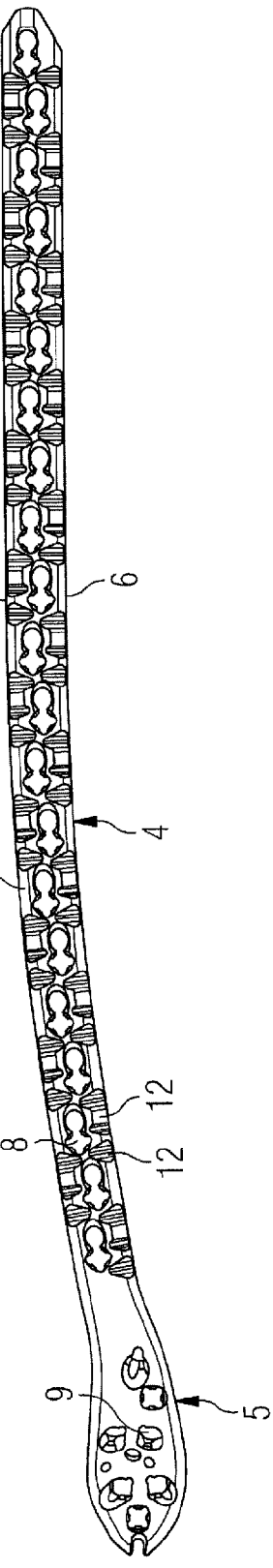

BONE PLATE

FIELD OF THE INVENTION

The present invention relates to the field of surgical devices. Specifically, the invention relates to a bone plate for fixing bone segments, in particular, the proximal femur of a patient.

BACKGROUND

For stabilizing and fixing fractures it is known to employ bone plates fixed on the bone by means of suitable fastening elements such as, for example, bone screws, along with pins, bolts or other bone anchors. To guarantee secure fixation of the bone fragments to each other and of the bone plate to the bone, the bone anchors must be incorporated into the bone precisely. In particular, the angles at which the bone anchors are driven into the bone are of great importance.

Hence, it is known, for example, from EP 1 741 397 A1 to provide bone plates with through holes having a variable-angle portion which allows a threaded head of a locking screw to be received and locked in a threaded bone plate hole at different angles relative to a hole axis of the threaded bone plate hole. The threaded bone plate hole may have rib-like or thread structures interrupted by recesses that extend radially away from the hole axis, whereby one or a plurality of the recesses extends in the direction of a longitudinally running side edge of the bone plate. However, a problem arises here that, in particular in the region of the recesses of the variable-angle through hole that extend in the direction toward the side edge, stress peaks may occur when a bending load is placed on the bone plate. Because a bone plate is usually attached to the side of the bone that is under stress, the stress peaks occur in particular on the plate's upper side, i.e., the surface of the bone plate that faces away from the bone, when the bone plate is mounted to the bone.

The object of the present invention is to provide a bone plate having a variable-angle through hole wherein stress peaks that occur in the region of the variable-angle through hole upon a bending load on the bone plate are reduced.

SUMMARY OF THE INVENTION

According to a first aspect of the invention, a bone plate has a first surface which, when the bone plate is positioned over the bone, faces the bone, and a second surface on a side of the bone plate opposing the first surface which, when the bone plate is positioned over the bone, faces away from the bone. The bone plate also comprises an elongate shaft portion having two longitudinally running lateral side walls extending between the first and second surfaces to connect longitudinal edges of the first and second surfaces. In the shaft portion at least one through hole extends through the bone plate from the first to the second surface. The through hole has a variable-angle portion with a hole axis and an inner surface with a rib-like structure. The rib-like structure is interrupted by recesses extending radially away from the hole axis, at least one of the recesses extending in the direction of one of the side walls. The rib-like structure can comprise a thread, threaded portions or a thread-like structure or ribs, grooves or the like which extend in planes perpendicular to the hole axis. The through hole is configured to receive a threaded head of a head locking screw in the rib-like structure interrupted by the recesses, at different angles to the hole axis, so that the head locking screw is preferably lockable at a desired angle relative to the hole axis.

The second, i.e. non-bone-facing, surface of the bone plate may have at least one depression which extends into a portion of the second surface between the side walls and the through hole, and spaced apart from one of the side walls. The depression and the at least one through-hole recess extending in the direction of the side wall overlap. In other words, the depression extends through a portion of the second surface at least partially surrounding the through hole. In one exemplary embodiment, the depression overlaps the through hole completely. Further preferably, the at least one depression is spaced from both side walls.

According to one exemplary embodiment, the depression, in particular when it overlaps the through hole completely, has a greater extension in a transverse direction of the bone plate than the through hole. Thus, the portions of the bone plate with a greater risk of breakage such as, for example, portions between a longitudinal edge of the plate and the through hole, can be lowered completely with regard to the second surface of the bone plate.

In an exemplary embodiment, the depression possesses a substantially rectangular shape in a plan view of the second surface of the bone plate. It will be appreciated that the corners of the depression can be rounded, the sides can be slightly curved, and opposing sides of the depression need not be completely parallel in plan view.

According to one exemplary embodiment, a bottom portion of the depression (e.g., a portion of the depression defining a depth of the depression) is planar. An edge portion of the depression may have an inclined or preferably curved cross-sectional profile. In particular, the edge portion of the depression may have a cross-sectional profile in a transverse direction of the bone plate that is more strongly inclined or curved than a cross-sectional profile of the edge portion in a longitudinal direction of the bone plate. Preferably, the inclined or curved edge portion of the depression and the through-hole recess extend in the direction of the side edge overlap According to one exemplary embodiment, the edge portion and the bottom portion pass into each other continuously at least in the region of the recess extending in the direction of the side edge. Such a continuous transition means that the depression has no edge. The transition is smooth and does not form a sharp bend in the depression. Stress peaks are thereby reduced compared with an angular transition.

A depth of the depression is chosen in dependence on the geometry of the bone plate preferably such that the distribution of the stress when a bending load is imposed on the bone plate is optimal, in particular so as to weaken stress peaks that occur. It will be appreciated that the depth of the depression is preferably chosen only up to a measure at which the weakening of the bone plate by the depression does not outweigh the advantage of the improved stress distribution.

According to another exemplary embodiment, the bone plate possesses a head portion which is shorter and wider than the shaft portion. This can be, for example, a bone plate for the femur or tibia or other load bearing long bone. Preferably, there are provided in the shaft portion at least three of the stated through holes with a variable-angle portion, with three of the through holes that are arranged closest to the head portion respectively overlapping one of the above-described depressions on the second surface of the bone plate. However, it will be appreciated that, depending on the case of application, only one or two, more than three, or all, of the through holes can also respectively overlap with a depression.

BRIEF DESCRIPTION OF THE DRAWINGS

The preceding summary of the invention as well as the following description of an exemplary embodiment will become more easily understandable in the light of the attached drawings. An exemplary embodiment of the invention will be described hereinafter with reference to the accompanying drawings. It will be appreciated, however, that the application is not limited to the exemplary embodiment shown.

FIG. 1 shows a top plan view of a bone plate, according to an exemplary embodiment of the present invention;

FIG. 2 shows a side view of the bone plate of FIG. 1;

FIG. 3 shows a bottom plan view of the bone plate of FIG. 1;

DETAILED DESCRIPTION

Figure 4:
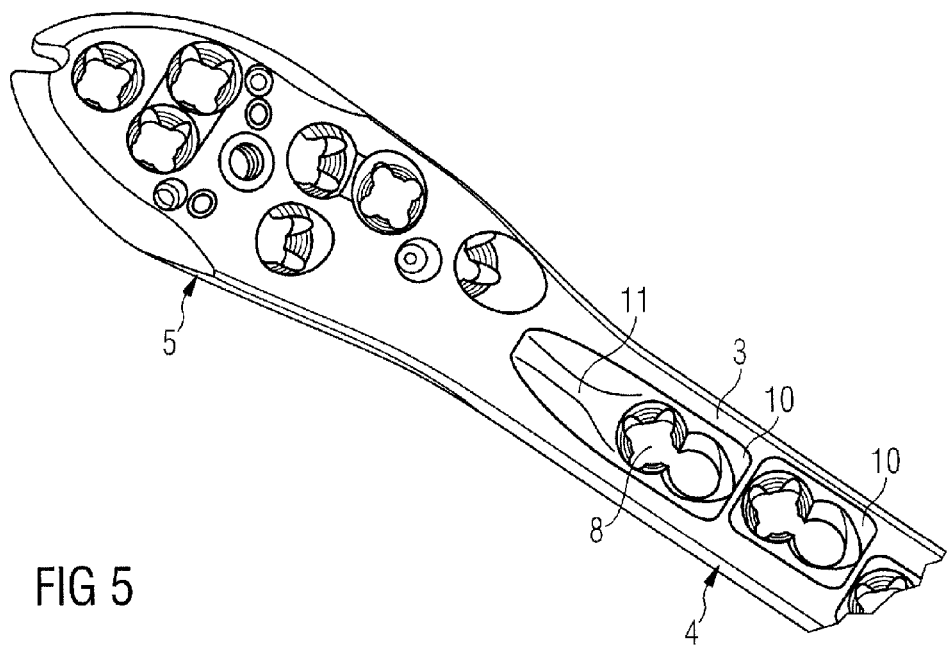
FIG. 4 shows a perspective view of a portion of the bone plate of FIG. 1.

The present invention may be further understood with reference to the following description and the appended drawings, wherein like elements are referred to with the same reference numerals. Exemplary embodiments of the present invention describe a bone plate for fixing fractures. In particular, the exemplary embodiments describes a bone plate including a depression extending through the bone plate and surrounding a through hole extending therethrough to reduce stress peaks, for example, along a portion of the between a through hole and a lateral side wall of the bone plate. Although the exemplary embodiments specifically describe a bone plate configured for the fixation of a proximal femur, it will be understood by those of skill in the art that the bone plate of the present invention may be adapted for the fixation of any of a variety of bones and, in particular, load bearing long bones.

FIG. 1 shows an exemplary embodiment of a bone plate 1 in plan view from an upper side—i.e., a first surface 3 of the bone plate 1 which, when the bone plate is implanted or positioned over a bone, faces away from the bone. The represented bone plate 1 is dimensioned for treating fractures of the left proximal femur, for example, of a human patient. It will be appreciated that the concepts described hereinafter are also applicable to other bone plates, in particular to a bone plate for the right proximal femur, the distal femur, or for other long bones , such as, for example, the tibia. In FIG. 2, the bone plate 1 is represented in a side view. FIG. 3 shows the bone plate 1 from an underside of the plate, i.e., from a second surface 2 which, when the bone plate is implanted or positioned over a bone, faces the bone.

Figure 5:
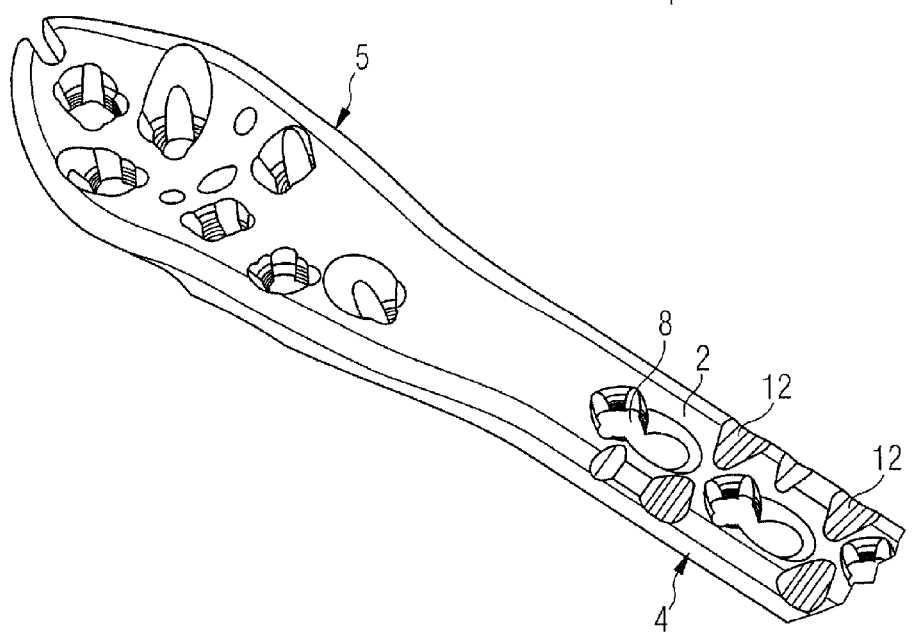
FIG. 5 shows a perspective view of a portion of the bone plate of FIG. 1.

The bone plate 1 comprises an elongate shaft portion 4 and a head portion 5 along with lateral side walls 6, 7 extending along the shaft portion 4 between the surfaces 2, 3 to define a width of the shaft portion 4. The width of the shaft portion 4 is substantially constant over a total length of the shaft portion 4. The head portion 5 is wider than the shaft portion 4, i.e., a distance between the surfaces 2, 3 is larger at the head portion 5 than at the shaft portion 4, and shorter than the shaft portion 4, i.e., a length of the head portion 5 along a longitudinal axis of the bone plate 1 is smaller than a length of the shaft portion 4 along the longitudinal axis of the bone plate. In one exemplary embodiment, the head portion 5 is preferably configured to adjoin the proximal femur, in particular, the greater trochanter. For example, the head portion 5 may have a curvature corresponding to the greater trochanter, as seen especially well in FIG. 2. The head portion 5 has a plurality of through holes 9, which may be formed here as variable-angle through holes and/or fixed angle through holes. In one exemplary embodiment, the head portion 5 may include, for example, seven through holes 9, three of which may be fixed angle through holes and the remaining through holes formed as variable angle through holes. It will be understood by those of skill in the art, however, that the plurality of through holes 9 may include any combination of variable angle and fixed angled through holes. The head portion 5 is also represented in FIGS. 4 and 5. FIG. 4 shows the head portion 5 in a perspective view from the first surface 3 of the bone plate 1, whereas FIG. 5 shows the head portion 5 of the bone plate 1 in a perspective view from the second surface 2 of the bone plate 1. The shaft portion 4 has an elongate shape and may include a slight curvature to correspond to the shape of the femur. It will be understood by those of skill in the art that a bone plate configured for the right proximal femur may have an accordingly opposite curvature.

Figure 8:
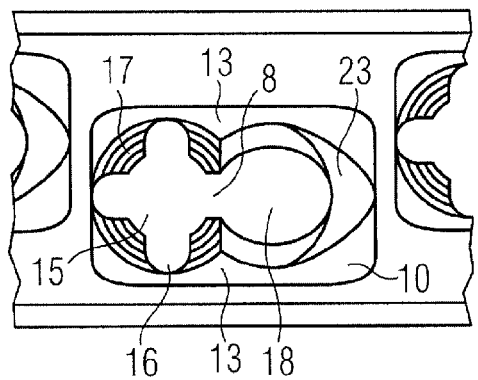
FIG. 8 shows a top plan view of a through hole extending through the bone plate of FIG. 1.

As represented in detail in FIG. 8, the through holes 8 in the shaft portion 4 are formed as combination holes. The through holes 8 have a variable-angle portion 15 as well as a compression hole 18. The variable-angle portion 15 possesses a rib- or thread-like structure 17 along an inner surface thereof, which tapers in a direction extending toward the bone-facing surface 2. The thread-like structure 17 is interrupted by recesses 16, which extend from the hole axis 19 radially outward. In the exemplary embodiment shown, there are formed four "columns" of the rib- or thread-like structure 17 which are separated from one another by the recesses 16. It will be understood by those of skill in the art, however, that the variable-angle portion 15 is not required to include four columns and may include, for example, 2 or more columns. As is known to the person skilled in the art, the variable-angle portion 15 is configured to receive a head locking screw which is introducible with its head thread into the variable-angle portion 15 of the through hole 8 at different angles, and lockable so that the screw is locked therewithin at a desired angle relative to the hole axis. The compression hole 18 has an unthreaded, i.e. smooth, inner surface 23 tapering in the direction of the bone-facing surface 2. The compression hole 18 is moreover elongated in the longitudinal direction of the shaft portion 4, so that the introduction of a compression screw with a smooth screw head therein causes a compression of the subjacent bone segments, as is known to the person skilled in the art.

Although the through hole 8 is described and shown as a combination hole including a variable angle 15 and compression hole portion 18, it will be understood by those of skill in the art that the through hole 18 may include other configurations. For example, the through hole 8 may include a locking hole portion and a compression hole portion open to one another. The locking hole portion may include, for example, a threading extending thereabout configured to lockingly receive a threaded head of a locking screw. The compression hole portion may be substantially similar to the compression hole portion 18 described above, including an unthreaded tapered surface for interfacing with a smooth head of a compression screw.

As is represented in FIG. 1, the first three through holes 8 along the shaft 4 that are closest in distance to the head portion 5, respectively overlap a depression 10 on the surface 3 of the plate's upper side. In other words, the depression 10 may extend through a portion of the bone plate 1 surrounding, or at least partially surrounding, the through hole 8. Although the exemplary embodiment specifically shows and describes three through holes 8 as including a depression 10 extending thereabout, it will be understood by those of skill in the art that any number of the through holes 8 may include a depression 10 extending thereabout. Furthermore, there is provided on the plate's upper side in the surface 3 a cavity 11 between the first through hole 8—i.e., the through hole 8 closest in distance to the head portion 5—and the head portion 5. On the second surface 2 there are arranged, as represented in FIG. 3, groups of recesses 12 along the length of the shaft portion 4. The depressions 10 and the cavity 11 are likewise represented in FIGS. 4 and 6. The recesses 12 are seen in detail in FIGS. 5 and 7. The depressions 10, the cavity 11 and the recesses 12 contribute both individually and in combination to reducing the risk of breakage of the bone plate 1, as described in detail hereinafter. Hence, it will be appreciated that the depressions 10, the cavity 11 and the recesses 12 can be provided in a bone plate separately or together.

Figure 9:
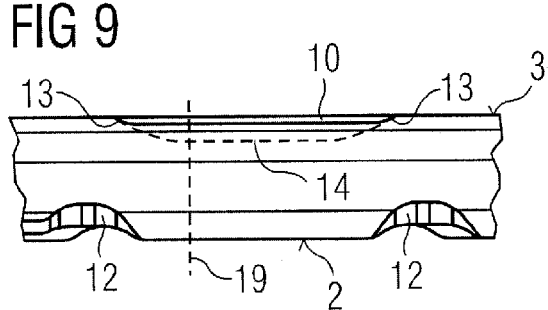
FIG. 9 shows a side view of the bone plate of FIG. 1, in the region of the through hole.
Figure 10:
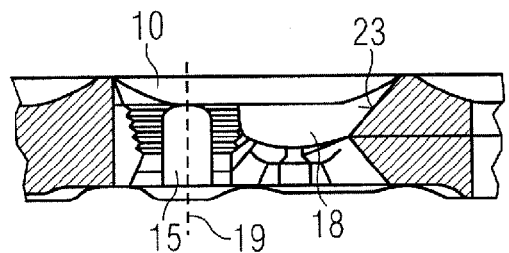
FIG. 10 shows a cross-sectional view of the bone plate of FIG. 1 along the line A-A in FIG. 6.

FIG. 8 shows the depression 10 in plan view of the plate's first surface 3. The depression 10 may have a substantially rectangular shape and completely overlaps the through hole 8 formed as a combination hole. In particular in the region of the recesses 16 of the variable-angle portion 15 of the through hole 8, which point in the direction of the lateral side walls 6, 7 of the shaft portion 4 of the bone plate 1, the provision of the depression 10 can reduce stress peaks that occur when a bending load or torsional load is imposed on the bone plate 1. The mouth of the through hole 8 is brought closer to a center plane of the bone plate 1 by the depression 10. The depression 10 can be produced, for example, by milling the surface 3 of the bone plate 1. The depression 10 has edge regions 13 which, in the represented embodiment, overlap with the recesses 16 which point in the direction of the side walls 6, 7. In FIG. 9 the depression 10 is represented in a side view of the bone plate 1. A bottom portion 14 (e.g., a portion defining a depth of the depression 10) is indicated by dashed lines. The bottom portion 14 may be substantially planar, whereas edge regions 13 may be curved. The edge regions 13 pass into the bottom region 14 smoothly. FIG. 10 shows a cross-section of the through hole 8 and the depression 10 in a section along the line A-A in FIG. 6. FIG. 10 also shows the variable-angle portion 15 which overlaps with the compression hole 18.

Figure 6:
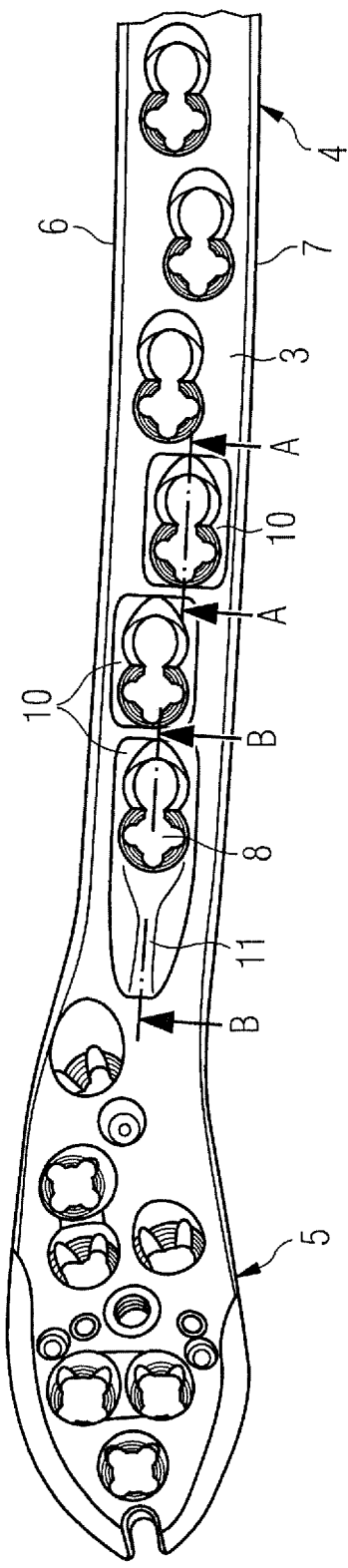
FIG. 6 shows an enlarged detailed view of the bone plate of FIG. 1.
Figure 11:
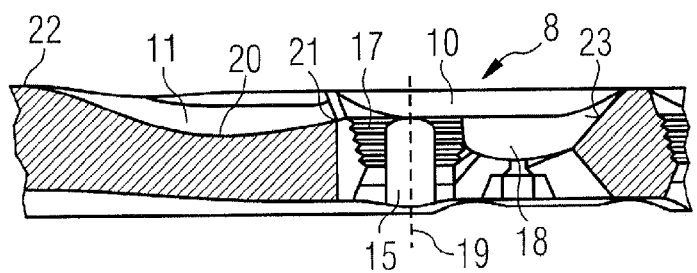
FIG. 11 shows a cross-sectional view of the bone plate of FIG. 1 along the line B-B in FIG. 6.

In FIG. 11 shows a cross-section of the bone plate 1 along the line B-B in FIG. 6. The sectional representation shows the first through hole 8, closest in distance to the head portion 5, which overlaps with the depression 10. As also represented in FIG. 6, the cavity 11 borders with its distal end 21 on the depression 10 of the first through hole 8. The depression 10 and the cavity 11 are open to one another at the end 21 of the cavity 11. The depression 10 and the cavity 11 may have the same width, in particular, at the place where they border on each other. This enables the cavity 11 and the depression 10 to be produced, for example milled, in one step. The cavity 11 serves to increase the flexibility of the region between the first through hole 8 and the head portion 5 of the bone plate 1, so as to reduce the risk of breakage of the bone plate in the region of the first through hole 8. In particular, the bone fracture can lie in the region of the bone plate 1 that lies between the first through hole 8 and the head portion 5, so that an especially high load acts on the bone plate 1 here.

As represented in FIG. 11, the cavity 11 has a curved cross-sectional profile. The depth of the cavity 11 increases continuously from the shaft portion 4 in the direction of the head portion 5 from the distal end 21 of the cavity 11 to a deepest point 20. In an exemplary embodiment, the depth of the cavity 11 decreases continuously from the deepest point 20 to a proximal end 22, with the cavity 11 tapering off relatively flat, that is to say, enclosing an angle, which in one embodiment, is smaller than 10° relative to the first surface 3 of the bone plate 1. As seen in FIGS. 4 and 6, the cavity 11 does not extend over the total width of the shaft portion 4 of the bone plate 1 (i.e., a distance between the lateral side walls 6, 7 of the bone plate), but is spaced from the side walls 6, 7. This retains a sufficient stability of the bone plate 1 in spite of the elevated flexibility caused by the cavity 11.

Figure 7:
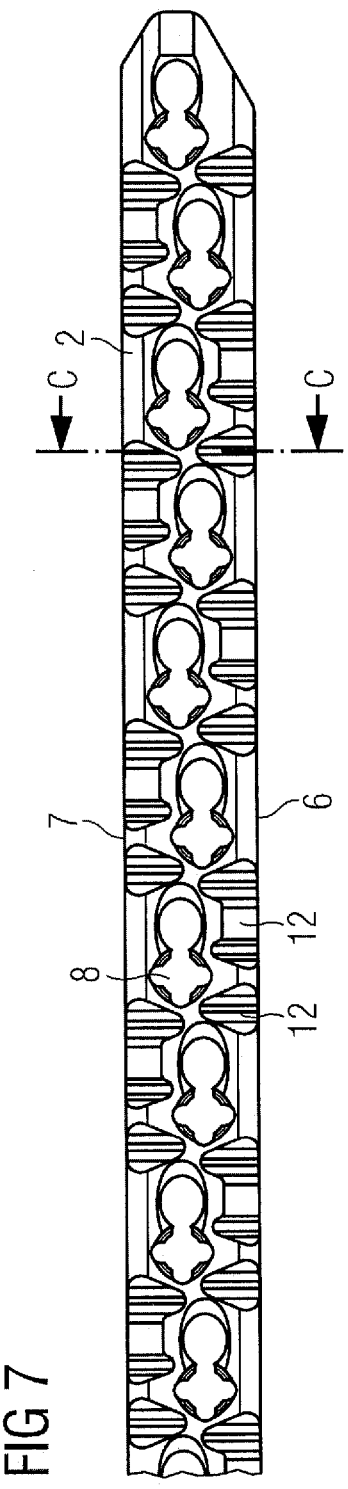
FIG. 7 shows an enlarged detailed view of the bone plate of FIG. 3.
Figure 12:
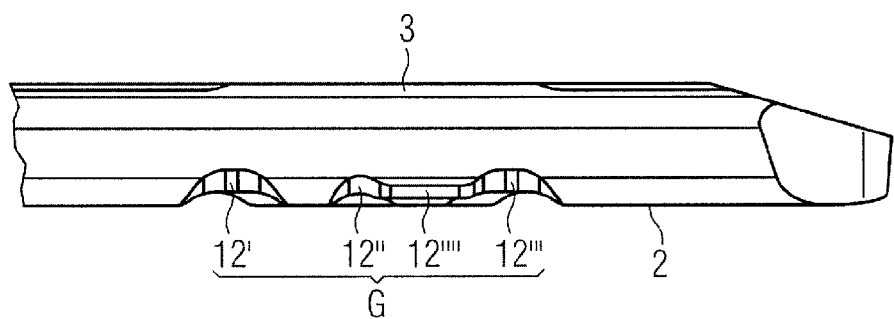
FIG. 12 shows a side view of a portion of the bone plate of FIG. 1.
Figure 13:
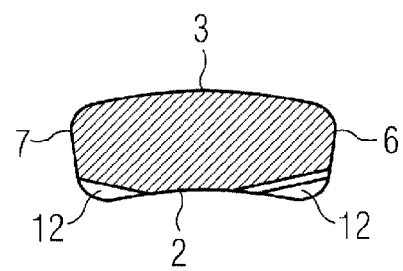
FIG. 13 shows a cross-sectional view of the shaft portion of the bone plate of FIG. 1, along the line C-C in FIG. 7.
Figure 14:
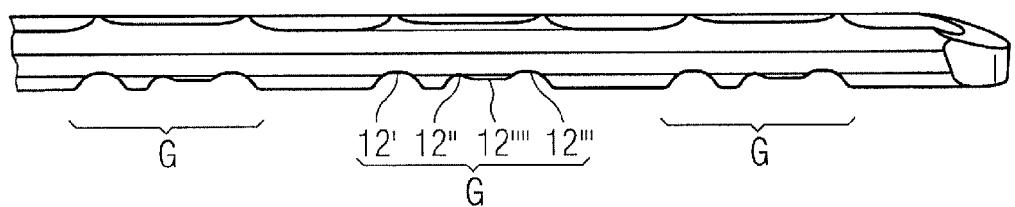
FIG. 14 shows a side view of the bone plate of FIG. 1, rotated by 10°.

In FIG. 12 there is represented a side view of the bone plate 1, in particular of the shaft portion 4, in which a group G of recesses 12 is to be seen. For the sake of better representability, FIG. 14 shows the shaft portion 4 in a view rotated by 10° about the longitudinal axis of the bone plate 1. FIG. 13 shows a cross-sectional view of the shaft portion 4 of the bone plate 1 along the line C-C in FIG. 7. As seen in FIGS. 7, 12 and 13, a group G of recesses 12 which is associated with one of the through holes 8 comprises four recesses 12', 12", 12''', 12'''', whereby in this embodiment not only a plurality, but all groups G have the identical four recesses 12', 12", 12''', 12'''' (except the first and the last group). In one exemplary embodiment, the first recess 12' and third recess 12''' are formed substantially identically, the second recess 12" being formed smaller. The fourth recess 12'''' connects the second and the third recess 12", 12''', so that these can alternatively also be regarded as a contiguous recess. As seen in FIG. 14, the recesses 12 extend from one of the side walls 6, 7 obliquely toward the center of the bone plate 1, having the greatest depth on the side wall 6, 7 of the bone plate 1. As seen in particular in FIG. 7, the groups G of recesses 12 are arranged alternately offset from each other on the opposing side walls 6, 7 of the shaft portion 4 of the bone plate 1 and in the direction of longitudinal extension of the shaft portion 4, with the opposing groups G of recesses 12 partly overlapping in the direction of longitudinal extension of the shaft portion 4. The arrangement of the groups G of recesses 12 corresponds to the arrangement of the through holes 8 along the longitudinal extension of the shaft portion 4. As seen in FIG. 7, the through holes 8 are arranged offset from each other alternately with respect to a center axis extending in the direction of longitudinal extension of the shaft portion 4. Accordingly, the groups G of recesses 12 are also arranged offset from each other alternately with regard to the center axis. Preferably, the cross-sectional area can respectively be formed along the longitudinal extension of the shaft portion 4 such that the section modulus of the shaft portion 4 is substantially constant along its longitudinal extension, but at least uniform, i.e. not subject to any great fluctuations. This avoids the highest stress upon a bending of the bone plate 1 occurring at a through hole 8. As seen in FIGS. 5 and 7, it will be appreciated that although the groups G of recesses 12 are preferably identical along the longitudinal extension of the shaft portion 4, the recesses 12 associated with the first through hole 8 (i.e., the through hole closest to the head portion 5) and the last through hole 8 (i.e., the through hole furthest from the head portion 5) are associated with a group G of recesses 12 which may not include all of the recesses 12', 12'', 12' and 12'''' described above, because the respective end of the shaft portion 4 is reached.

Although the preferred embodiment was described with reference to a left or right proximal femur, it will be appreciated that the principle of the invention can also be applied to bone plates for other bones. For example, the invention can also be employed for the distal femur, the tibia or other load bearing long bones. It will be appreciated that the shape and dimensioning of the bone plate can be adapted in accordance with the case of application without impairing the principle of the invention.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A bone plate having a first, bone-facing surface on a first side, and a second surface on a second side opposing the first side, the bone plate comprising;
   an elongate shaft portion having two lateral side walls extending between the first surface and the second surface to connect longitudinal edges of the first and second surfaces;
   at least one through hole extending through the elongate shaft from the first surface to the second surface, the through hole configured to receive a bone fixation element therein;
   at least one depression extending into the second surface about at least a portion of a periphery of the through hole in a portion of the second surface between the side walls and the through hole; and
   at least one recess extending into the first surface from a side wall obliquely toward the through hole, the recess having a greatest depth at the side wall.

2. The bone plate according to claim 1, wherein the depression extends about an entire periphery of the through hole.

3. The bone plate according to claim 1, wherein the at least one depression is spaced from both side walls.

4. The bone plate according to claim 1, wherein the depression has a greater extension in a transverse direction of the bone plate than the through hole.

5. The bone plate according to claim 1, wherein the at least one depression has a substantially rectangular shape in plan view of the second surface of the bone plate.

6. The bone plate according to claim 1, wherein the depression is defined by a bottom portion and an edge portion.

7. The bone plate according to claim 6, wherein the edge portion has a curved cross-sectional profile.

8. The bone plate according to claim 6, wherein the bottom portion of the depression is substantially planar.

9. The bone plate according to claim 6, wherein the edge portion and the bottom portion are connected to define a smooth surface of the depression.

10. The bone plate according to claim 1, wherein the bone plate has a thickness between the first surface and the second surface in a cross-sectional profile, cutting the through hole, of the bone plate in a transverse direction of the bone plate, and the depression has a depth that amounts to up to 50% of the thickness of the bone plate.

11. The bone plate according to claim 1, wherein the bone plate has a head portion which is shorter and wider than the shaft portion, the at least one depression on the second surface of the bone plate extending about a through hole arranged closest to the head portion.

12. The bone plate according to claim 1, wherein the through hole is formed as part of a combination hole which includes a compression hole, the compression hole being formed elongately in a longitudinal direction of the shaft portion and having an unthreaded inner surface tapering in the direction of the first, bone-facing surface.

13. The bone plate according to claim 12, wherein the through hole further comprises a variable-angle portion overlapping with the compression hole portion, the variable-angle portion configured to receive a threaded head of a locking screw at a desired angle within a permitted range of angulation relative to a hole axis.

14. The bone plate according to claim 13, wherein the variable-angle portion of the through hole tapers in the direction of the first, bone-facing surface of the bone plate.

15. The bone plate according to claim 12, wherein the through hole further comprises a locking hole portion including a threading extending thereabout configured to lockingly receive a correspondingly threaded head of a locking screw.

16. A bone plate having a first, bone-facing surface on a first side, and a second surface on a second side opposing the first side, the bone plate comprising;
   an elongate shaft portion having two lateral side walls extending between the first surface and the second surface to connect longitudinal edges of the first and second surfaces;
   at least one through hole extending through the elongate shaft from the first surface to the second surface, the through hole configured to receive a bone fixation element therein; and
   at least one depression extending into the second surface about at least a portion of a periphery of the through hole in a portion of the second surface between the side walls and the through hole,
   wherein the depression is defined by a bottom portion and an edge portion, and
   wherein the edge portion of the depression and a through hole recess extending in the direction of the side wall overlap.

* * * * *